(12) United States Patent
Mendell

(10) Patent No.: US 6,450,945 B1
(45) Date of Patent: Sep. 17, 2002

(54) SYSTEM AND METHOD FOR TREATMENT OF INFERTILITY

(76) Inventor: Sherwin G. Mendell, 1495 Seabay Rd., Weston, FL (US) 33326

( * ) Notice: Subject to any disclaimer, the term of this patent is extended or adjusted under 35 U.S.C. 154(b) by 33 days.

(21) Appl. No.: 09/785,776

(22) Filed: Feb. 20, 2001

(51) Int. Cl.⁷ ............................................. A61M 21/00

(52) U.S. Cl. ...................... 600/26; 600/547; 600/548; 606/204; 128/907

(58) Field of Search .................... 600/26, 547, 548; 606/201, 204; 128/898, 907

(56) References Cited

U.S. PATENT DOCUMENTS

| | | | |
|---|---|---|---|
| 5,773,416 A | | 6/1998 | Chehab |
| 6,152,140 A | * | 11/2000 | Blum ........................ 128/898 |
| 6,237,603 B1 | * | 5/2001 | Mendell ..................... 128/897 |

OTHER PUBLICATIONS

Beal, M.W., Women's use of complementary and alternative therapies in reproductive health care., May–Jun. 1998, PubMed, Nurse Midwifery, 224–34.*

Aikins Murphy P., Alternative therapies for nausea and vomiting of pregnancy., Jan. 1991, PubMed, Obstet Gynecol, 149–55.*

* cited by examiner

Primary Examiner—Timothy L. Maust
(74) Attorney, Agent, or Firm—Alvin S. Blum

(57) ABSTRACT

A method of treatment for infertility includes hypnotic suggestions of relaxation and feelings of being pregnant. Also included are acupressure applied to specific selected body sites, and application of a large area magnet to the body surface over the uterus. The acupressure may be applied by acupuncture needles, pressure applied by small blunt sticks, laser light, electro-stimulation, or small strong magnets. The method may be applied by a practitioner. In another embodiment of the invention, the materials are supplied in a kit form including audio and video recordings and implements for application of acupressure by the patient herself.

1 Claim, 3 Drawing Sheets

FIG.4
FIG. 5
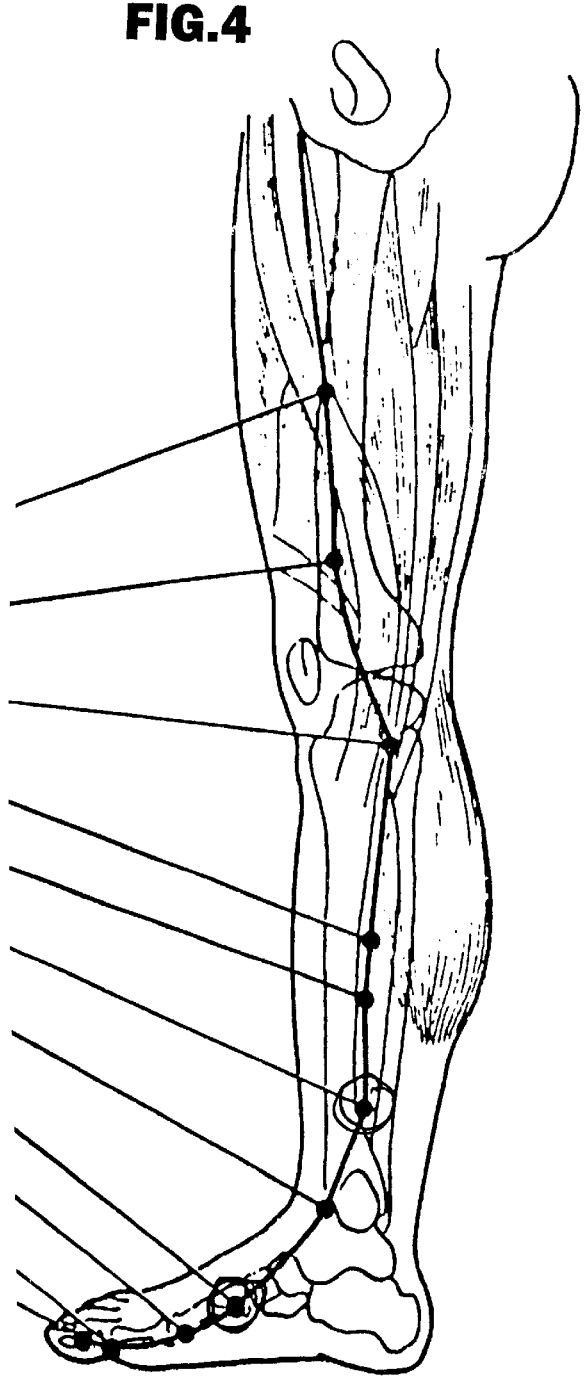
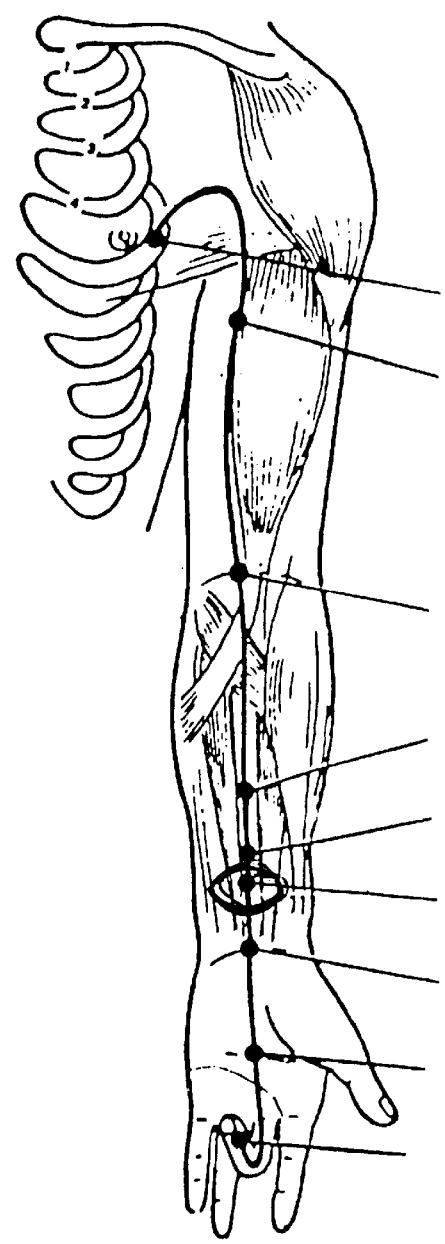

SYSTEM AND METHOD FOR TREATMENT OF INFERTILITY

BACKGROUND OF THE INVENTION

This invention relates to infertility and more particularly to a system and a method of enhancing a woman's chances of conceiving a child.

DESCRIPTION OF THE PRIOR ART

It is well known that some women have great difficulty in becoming pregnant. U.S. Pat. No. 5,773,416 issued Jun. 30, 1998 to Chehab reviews some of the concepts related to infertility. It states that while a variety of treatments have been proposed for lack of fertility, none have been entirely successful, and there remains a need for identifying improved and/or alternative therapies for enhancing fertility. Improved methods should be effective, have minimal side effects, be compatible with other treatments, and contribute to conception. It is well known that an infertile woman may more easily become pregnant after adopting a child. The fertility system is very complex. It involves the brain, which acts on the hypothalamus. This in turn acts on the pituitary, which releases gonadotropins that act on the gonads. Much of the process remains a mystery, but we can assume that the brain is at least a partial mediator in the process of conception.

SUMMARY OF THE INVENTION

It is accordingly an object of the invention to provide a method and system for treatment of infertility in women that has little or no side effects. It is another object of the invention that the method and system be compatible with other therapies such as the administration hormones.

The system of the invention comprises:

1) hypnosis of the patient with particular suggestions related to relaxation and the feelings of actually being pregnant;
2) acupressure or acupuncture at prescribed body sites with the use of conventional acupuncture needles, acupressure using blunt objects, concentrated light sources, electrical stimuli or small magnets; and
3) application of large magnets to prescribed body sites.

This system does not include the administration of any materials into the body. Consequently the chance of side effects is greatly diminished and there is no interaction with agents such as hormones that might be desirable to administer during the course of this treatment. Because many of these women are feeling the biological clock ticking away, a treatment that does not interfere with conventional drug administration has a greater chance of acceptance and success compared to therapy that requires suspension of conventional treatment that may delay treatment until menopause is reached.

In a first embodiment of the invention, the system may be practiced on a patient by a practitioner. In another embodiment of the invention, materials are supplied in kit form to be sent to the patient for at-home use by the patient herself. The kit may include audio recordings of the hypnotherapy; video recordings of the placement of the acupressure devices; acupressure devices such as small blunt sticks, electro-stimulators, small magnets, laser lights, and the like; printed instructions and charts of recommended acupressure sites; and large area magnets.

These and other objects, features, and advantages of the invention will become more apparent when the detailed description is studied in conjunction with the drawings.

BRIEF DESCRIPTION OF THE DRAWINGS

FIG. 4 is a chart of specific sites on each leg that are recommended for this acupressure treatment.

FIG. 5 is a chart of a specific site on each arm that is recommended for this acupressure treatment.

DETAILED DESCRIPTION OF PREFERRED EMBODIMENTS OF THE INVENTION

Figure 1:
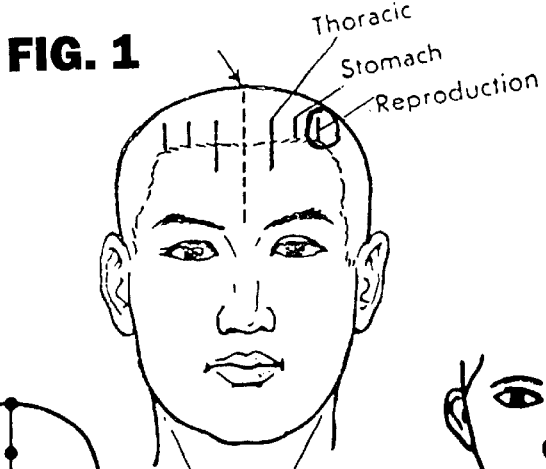
FIG. 1 is a chart of a specific site on the head that is recommended for this acupressure treatment.
Figure 2:
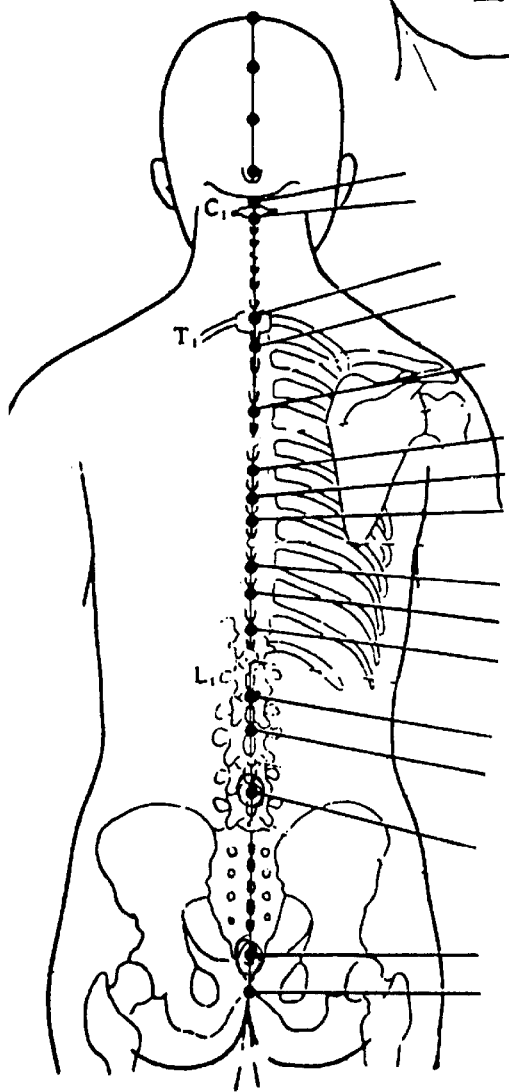
FIG. 2a is a chart of specific sites on the front of the torso that are recommended for this acupressure treatment.
FIG. 2b is a chart of specific sites on the rear of the torso that are recommended for this acupressure treatment.
Figure 2:
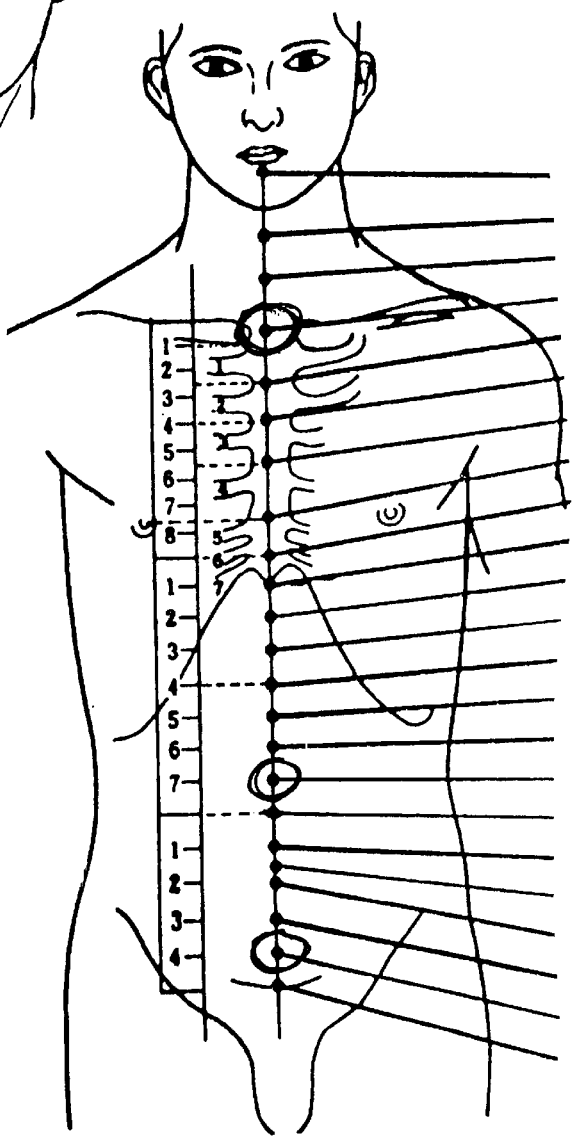
Figure 6:
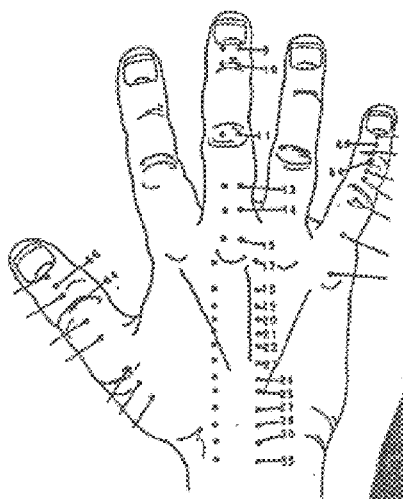
FIG. 6a is a chart of specific sites on the dorsum of each hand that are recommended for this acupressure treatment.
FIG. 6b is a chart of specific sites on the palm of each hand that are recommended for this acupressure treatment.
Figure 6:
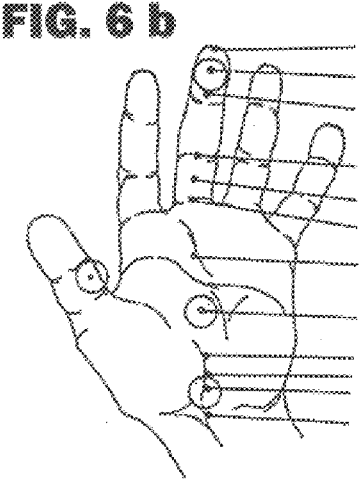
Figure 3:
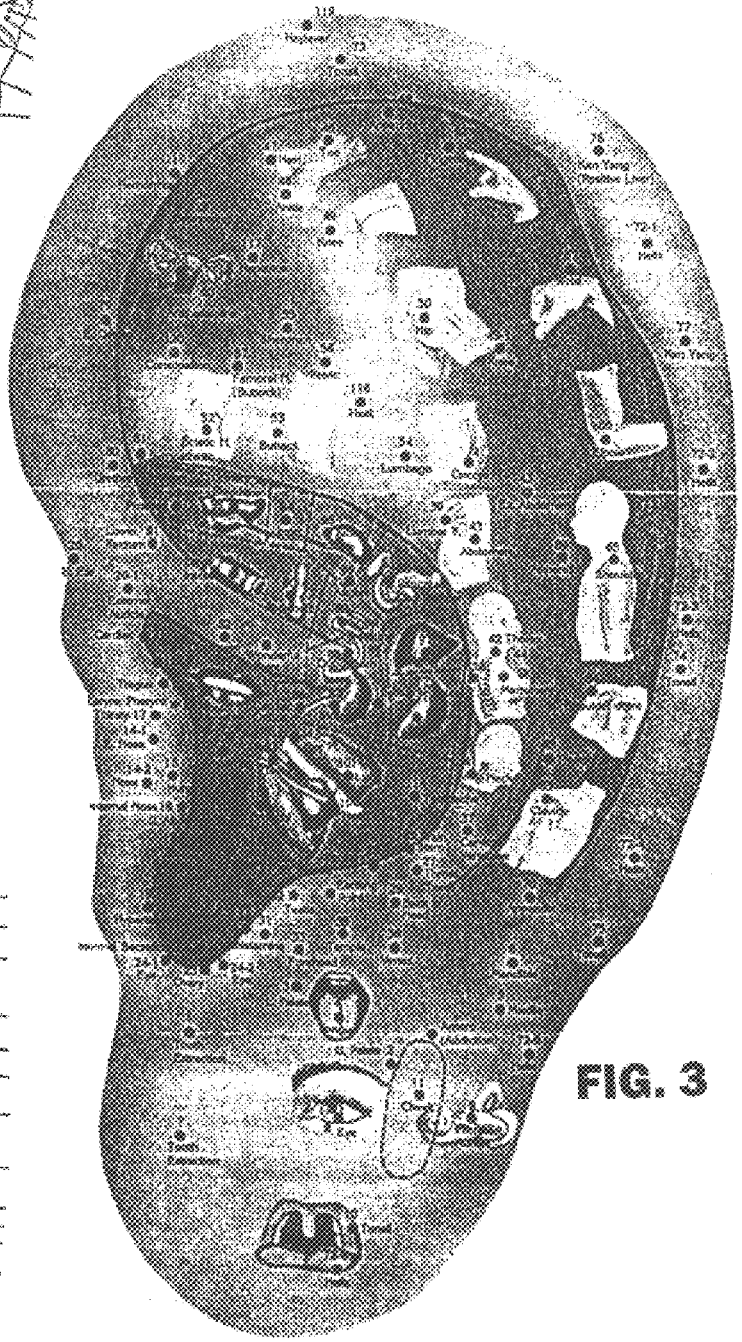
FIG. 3 is a chart of specific sites on each ear that are recommended for this acupressure treatment.

The invention comprises a method of enhancing conception in a woman having difficulty in becoming pregnant. The method comprises the steps of: inducing a relaxation and feelings of being pregnant by hypnosis; applying acupressure to selected body sites; and application of large area magnets to the body surface over the uterus, ovaries, and pelvic nerve plexus. The hypnotic suggestions and acupressure may be used in combination without the application of the large area magnet. It is felt that the large area magnet improves the chances of success of the method. The acupressure may be applied by conventional acupuncture needles. Alternatively, the acupressure may be applied by: a simple small diameter blunt implement such as the end of a swizzle stick; by a concentrated light source such as a laser pointer; by a small diameter, such as $3/8$ inches, magnet; or a small, gentle electro-stimulator such as Pointer Plus from OMS MEDICAL SUPPLIES, Braintree, Mass. The large area magnet may be at least 8 square inches in area, a 2 inch by 6 inches square magnet, ½ inch thick has been found to be effective, a 3 inch diameter discoidal magnet has also been found to be effective. The magnets are applied with the south pole against the body surface. The small magnets should be at least 100 gauss and the large magnets at least 1000 gauss. The magnets may be taped in place or supplied with pressure sensitive adhesive on the south face to keep them in place and to ensure correct placement.

Referring now to the drawings, the drawing are conventional acupuncture charts on which the acupuncture sites that have been found to be effective for this purpose have been circled. While I have shown and described the preferred embodiments of my invention, it will be understood that the invention may be embodied otherwise than as herein specifically illustrated and described, and that certain changes in form and arrangement of parts and the specific manner of practicing the invention may be made within the underlying idea or principles of the invention.

What is claimed is:

1. A system for treatment of infertility in women in the form of a kit to be used by the woman the kit comprising:
   a) audio and video recordings;
   b) printed instructions;
   c) charts of selected acupressure sites;
   d) acupressure implements for applying acupressure to the selected sites;
   e) at least one large area magnet having a surface area of at least 8 square inches;

f) the kit enabling the user woman to practice by herself the method of treatment of infertility comprising the steps of:
  5i) induction of relaxation and feelings of being pregnant by hypnotic suggestion through listening to the audio recording;
  ii) application of acupressure at selected body sites shown in the video recording and charts employing at least one of means of application supplied with the kit selected from the group comprising: acupuncture needles; small blunt objects; concentrated light sources; electro-stimulators; and small area magnets; and
  iii) application of a large area magnet having an area of at least 8 square inches to the body surface in the area above the uterus.

\* \* \* \* \*